United States Patent
Delay-Goyet et al.

(10) Patent No.: US 8,592,443 B2
(45) Date of Patent: Nov. 26, 2013

(54) USE OF 4 CYCLOPROPYLMETHOXY-N-(3,5 DICHLORO-1 OXIDO-PYRIDIN-4 YL)-5-(METHOXY)PYRIDINE-2-CARBOXAMIDE FOR THE TREATMENT OF SPINAL CORD TRAUMAS

(75) Inventors: Philippe Delay-Goyet, Paris (FR); Badia Ferzaz, Paris (FR); Jocelyne Lolivier, Paris (FR)

(73) Assignee: Sanofi, Paris (FR)

( * ) Notice: Subject to any disclaimer, the term of this patent is extended or adjusted under 35 U.S.C. 154(b) by 24 days.

(21) Appl. No.: 12/573,316

(22) Filed: Oct. 5, 2009

(65) Prior Publication Data

US 2010/0137370 A1 Jun. 3, 2010

Related U.S. Application Data

(63) Continuation of application No. PCT/FR2008/000533, filed on Apr. 16, 2008.

(30) Foreign Application Priority Data

Apr. 19, 2007 (FR) ..................... 07 02851

(51) Int. Cl.
*A01N 43/40* (2006.01)
*A61K 31/435* (2006.01)

(52) U.S. Cl.
USPC ........................................ 514/277

(58) Field of Classification Search
USPC ................................ 514/335, 277
See application file for complete search history.

(56) References Cited

U.S. PATENT DOCUMENTS

| 4,193,926 | A | 3/1980 | Schmiechen et al. |
| 6,177,077 | B1 * | 1/2001 | Tobinick .................... 424/134.1 |
| 6,472,412 | B1 * | 10/2002 | Fenton et al. ................. 514/348 |
| 7,045,660 | B2 | 5/2006 | Fenton et al. |
| 7,652,144 | B2 | 1/2010 | Fenton et al. |
| 8,129,537 | B2 | 3/2012 | Fenton et al. |
| 2003/0069169 | A1 | 4/2003 | Macor et al. |
| 2007/0021451 | A1 | 1/2007 | Kazui et al. |

FOREIGN PATENT DOCUMENTS

| GB | 2406856 | 4/2005 |
| JP | 2003519139 | 6/2003 |
| JP | 2005506286 | 3/2005 |
| WO | WO 95/04045 | 2/1995 |
| WO | WO 95/20578 | 8/1995 |
| WO | WO 96/31476 | 10/1996 |
| WO | WO 00/15116 | 12/2000 |
| WO | WO 01/47915 | 7/2001 |
| WO | WO 02/069905 | 9/2002 |
| WO | WO 2004/005258 | 1/2004 |
| WO | WO 2004/067006 | 8/2004 |
| WO | WO 2006/135828 | 12/2006 |

OTHER PUBLICATIONS

Barneoud, P., et. al, Quantitative Motor Assessment in Fals Mice: A Longitudinal Study, Neuroreport, vol. 8, pp. 2861-2865, (1997).
Nikulina, E., et. al., The Phosphodiesterase Inhibitor Rolipram Delivered After a Spinal Cord Lesion Promotes Axonal Regeneration and Functional Recovery, Proceedings of the National Academy of Sciences of the United States of America, vol. 101, No. 23, pp. 8786-8790, (2004).
U.S. Appl. No. 12/573,326, filed Oct. 5, 2009, Delay-Goyet et al.
U.S. Appl. No. 12/573,322, filed Oct. 5, 2009, Delay-Goyet et al.
U.S. Appl. No. 12/573,326—Office Action Dated Jul. 23, 2010.
Berk, C., et al., Thalamic Deep Brain Stimulation for the Treatment of Tremor Due to Multiple Sclerosis: A Prospective Study of Tremor and Quality of Life, J. Neurosurg, vol. 97, pp. 815-320, (2002).
U.S. Appl. No. 12/573,322—Office Action Dated Jul. 29, 2010.
Menniti, et al., Phosphodiesterases in the CNS: Targets for Drug Development, Nature Reviews, vol. 5, (2006), pp. 660-670.
U.S. Appl. No. 12/573,226—Office Action Dated Dec. 10, 2010.
Robichaud, et al., Emesis Induced by inhibitors of Type IV Cyclic Nucleotide Phosphodiesterase (PDE IV) in the Ferret, Neuropharmacology, vol. 38, (1999), pp. 289-297.
International Search Report for WO2008/145840 dated Dec. 4, 2008.
Houslay, et al., Phosphodiesterase-4 as a Therpaeutic Target, DDT, vol. 10, No. 22, (2005), pp. 1503-1519.
Sawanishi, et al., Selective inhibitors of Cyclic AMP-Specific Phosphodiesterase: Heterocycle-Condensed Purines, J. Med. Chem., (1997), vol. 40, pp. 3248-3253.
He, et al., Novel Cyclic Compounds as Potent Phosphodiesterase 4 Inhibitors, J. Med. Chem vol. 41, pp. 4216-4223, (1998).
Burnolie, et al., Synthesis, Structure-Activity Relationships, and Pharmacological Profile of 9-Arnino-4-oxo-l-phenyl-3,4,6,7-tetrahydro[1,41diazepino[6,7,1-hi]indoles: Discovery of Potent, Selective Phosphodiesterase Type 4 Inhibitors, J. Med. Chem., (2000), vol. 43, pp. 4850-4867.
Aoki, et al., Effect of a Novel Anti-Inflammatory Compound, YM976, on Antigen-induced Eosinophil Infiltration into the Lungs in Rats, Mice, and Ferrets, The Journal of Pharmacology and Experimental Therapeutics, (2000), vol. 295, No. 3, pp. 1149-1155.

* cited by examiner

*Primary Examiner* — Yong Chong
(74) *Attorney, Agent, or Firm* — Jiang Lin

(57) ABSTRACT

The present invention relates to the use of 4-cyclopropyl-methoxy-N-(3,5-dichloro-1-oxidopyridin-4-yl)-5-(methoxy)pyridine-2-carboxamide, in the form of a hydrate, of a solvate, of a base or of an addition salt with an acid, for the preparation of a medicament for use in the treatment of spinal cord traumas.

2 Claims, No Drawings

USE OF 4 CYCLOPROPYLMETHOXY-N-(3,5 DICHLORO-1 OXIDO-PYRIDIN-4 YL)-5-(METHOXY)PYRIDINE-2-CARBOXAMIDE FOR THE TREATMENT OF SPINAL CORD TRAUMAS

This application is a Continuation of International Application No. PCT/FR2008/000533, filed Apr. 16, 2008, which is incorporated herein by reference in its entirety.

The present invention relates to the use of 4-cyclopropylmethoxy-N-(3,5-dichloro-1-oxidopyridin-4-yl)-5-(methoxy)pyridine-2-carboxamide, in the form of a hydrate, of a solvate, of a base or of an addition salt with an acid, for the preparation of a medicament for use in the treatment of spinal cord traumas.

4-Cyclopropylmethoxy-N-(3,5-dichloro-1-oxidopyridin-4-yl)-5-(methoxy)pyridine-2-carboxamide, alternatively called N-(3,5-dichloro-1-oxido-4-pyridinio)-4-cyclopropylmethoxy-5-methoxypyridine-2-carboxamide, is known to be part of the composition of medicaments for use in the treatment of various pathologies, including in particular inflammations of the joints, arthritis and rheumatoid arthritis. This compound, in hemihydrate form, is described, for example, in document WO 95/04045 (compound referenced FR).

There exists a need to find medicaments for treating patients suffering from spinal cord traumas. Studies have shown, in animals, that a possible approach is the administration of compounds which inhibit phospho-diesterases 4 (PDE 4), such as, for example, rolipram. However, clinical studies have shown that this compound, and also other inhibitors of PDE 4, induce emetic effects which do not allow it to be used in therapy.

It has now been found that 4-cyclopropylmethoxy-N-(3,5-dichloro-1-oxidopyridin-4-yl)-5-(methoxy)pyridine-2-carboxamide can be used in the treatment of spinal cord traumas while at the same time avoiding the emetic effects at therapeutically acceptable doses.

A first subject of the invention therefore relates to the use of 4-cyclopropylmethoxy-N-(3,5-dichloro-1-oxidopyridin-4-yl)-5-(methoxy)pyridine-2-carboxamide for the preparation of a medicament for use in the treatment of spinal cord traumas.

According to one embodiment of the invention, the use of 4-cyclopropylmethoxy-N-(3,5-dichloro-1-oxidopyridin-4-yl)-5-(methoxy)pyridine-2-carboxamide can be carried out with the latter in the form of a base or of an addition salt with an acid.

The salts that can be used in the context of the invention can be prepared with pharmaceutically acceptable acids, but the salts of other acids that are useful, for example, for the purification or the isolation of 4-cyclopropylmethoxy-N-(3,5-dichloro-1-oxidopyridin-4-yl)-5-(methoxy)pyridine-2-carboxamide are also part of the invention.

The use of 4-cyclopropylmethoxy-N-(3,5-dichloro-1-oxidopyridin-4-yl)-5-(methoxy)pyridine-2-carboxamide according to the invention can also be carried out with the latter in the form of a hydrate or of a solvate. The term "hydrate or solvate" is intended to mean the association or the combination of one or more molecules of 4-cyclopropylmethoxy-N-(3,5-dichloro-1-oxidopyridin-4-yl)-5-(methoxy)pyridine-2-carboxamide with one or more molecules of water or of solvent.

For the purpose of the present invention, the term "spinal cord trauma" is intended to mean acute or chronic pathologies which have an external origin and which destroy the spinal tract and/or neurons, and which occur, for example, during a fall, an impact, crushing or a road accident.

A second subject of the invention relates to a pharmaceutical composition comprising 4-cyclopropylmethoxy-N-(3,5-dichloro-1-oxidopyridin-4-yl)-5-(methoxy)pyridine-2-carboxamide as active ingredient and one or more pharmaceutically acceptable excipients.

The composition used according to the invention comprises an effective dose of the active ingredient.

For example, the daily doses of active ingredient that can be used according to the invention are from 0.001 to 10 mg/day.

According to the usual practice, the dosage appropriate for each patient is determined by the physician according to the method of administration and the age, weight and response of said patient.

The doses depend on the desired effect, on the duration of treatment and on the route of administration used.

There may be specific cases where higher or lower dosages are appropriate. Such dosages do not depart from the context of the invention.

The excipients are chosen, according to the pharmaceutical form and the method of administration desired, from the usual excipients which are known to those skilled in the art.

The composition may be administered orally, parenterally (including intrathecally) or rectally.

Suitable unit administration forms comprise oral administration forms, such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular, intravenous or intrathecal administration forms, rectal administration forms, and implants. For topical application, the active ingredients according to the invention may be used in creams, gels, ointments or lotions.

When a composition is prepared in tablet form, the active ingredient is mixed with one or more pharmaceutical excipients, such as gelatin, starch, lactose, magnesium stearate, talc, silica, gum arabic, mannitol, microcrystalline cellulose, hypromellose, or the like.

The tablets may be coated with sucrose, with a cellulosic derivative or with other substances suitable for coating. The tablets may be produced by various techniques, such as direct compression, dry or wet granulation, or hot melt.

It is also possible to obtain a pharmaceutical composition in the form of a gel capsule by mixing the active ingredient with a diluent and transferring the mixture obtained into soft or hard gel capsules.

For parenteral administration, use is made of aqueous suspensions, isotonic saline solutions or sterile injectable solutions which contain pharmacologically compatible agents, for example propylene glycol or butylene glycol.

By way of example, a unit administration form of 4-cyclopropylmethoxy-N-(3,5-dichloro-1-oxidopyridin-4-yl)-5-(methoxy)pyridine-2-carboxamide in tablet form comprises the following ingredients:

| | |
|---|---|
| 4-Cyclopropylmethoxy-N-(3,5-dichloro-1-oxidopyridin-4-yl)-5-(methoxy)pyridine-2-carboxamide | 1 mg |
| Mannitol | 224 mg |
| Sodium croscarmellose | 5 mg |
| Maize starch | 15 mg |
| Hydroxypropylmethylcellulose | 2 mg |
| Magnesium stearate | 3 mg |

The effects of 4-cyclopropylmethoxy-N-(3,5-dichloro-1-oxidopyridin-4-yl)-5-(methoxy)pyridine-2-carboxamide used according to the invention were evaluated in a model of spinal trauma in the mouse using the beam balance test (P. Barnéoud, NeuroReport 1997, 8, 2861-2865).

EXAMPLE 1

Evaluation of the effectiveness of 4-cyclopropyl-methoxy-N-(3,5-dichloro-1-oxidopyridin-4-yl)-5-(methoxy)pyridine-2-carboxamide in the treatment of spinal cord traumas:

The Beam Balance test consists in placing the mouse at the end of a horizontal beam 30 cm long and 1.5 cm wide, raised 20 cm above the ground. The time required for the mouse to reach the opposite end of the beam is measured. The test is stopped after 12 seconds. If the animal falls or does not accomplish the test, the maximum time is noted.

34-week-old female OF1 mice (Iffa Credo Lyon, France) weighing 12 to 14 g are placed in experimental cages (32× 21×14 cm) provided with an endless supply of food and water, at the controlled temperature of 22±1° C.

An experiment using the Beam Balance test is carried out in order to evaluate the effectiveness of 4-cyclopropyl-methoxy-N-(3,5-dichloro-1-oxidopyridin-4-yl)-5-(methoxy)pyridine-2-carboxamide in the treatment of spinal cord trauma.

The mice are subjected to a pre-learning phase which allows them to become familiar with the evaluation test and allows them to reach an optimal and identical level of performance.

The animals are subsequently divided up into three groups, and then a trauma is induced in a controlled manner in two of the three groups of mice before the beginning of the test phase.

This trauma consists of a lesion of the spinal cord located at the level of the thoracic vertebra Th8. The lesion is generated by 3 successive cycles of freezing-thawing by applying liquid nitrogen.

The functional consequences of the trauma are then measured at days 2, 7, 14 and 21 and also at day 28.

The following groups were formed:

Group 1 (no trauma) is composed of control animals which are not subjected to any trauma.

Group 2 (trauma alone) is composed of traumatized animals to which one dose per day of carrier (methylcellulose (MC) (0.6%) +tween-80 (0.5%) in water) is administered.

Group 3 (trauma+active ingredient 0.01 mg/kg at +4 hours) receives a solution containing 4-cyclopropylmethoxy-N-(3,5-dichloro-1-oxidopyridin-4-yl)-5-(methoxy)pyridine-2-carboxamide (0.01 mg/kg) in the carrier (MC (0.6%)+tween-80 (0.5%) in water), orally, 4 hours after the lesion, and then daily, orally, for 4 weeks after the trauma.

The results obtained for each group of mice are reported in Table 1:

TABLE 1

Results of the balance beam test for groups 1 to 3

| Groups | Results (seconds) | | | | | |
|---|---|---|---|---|---|---|
| | D − 4 | D = 0 Trauma | D + 2 | D + 7 | D + 14 | D + 21 | D + 28 |
| 1 (no trauma) | 3.95 | No | 3.52 | 3.77 | 3.25 | 2.99 | 2.92 |
| 2 (trauma alone) | 3.67 | Yes | 12.11 | 10.60 | 9.58 | 8.33 | 8.11 |
| 3 (trauma + active ingredient at +4 h) | 3.93 | Yes | 10.71 | 8.67 | 6.35 | 6.17 | 5.18 |

Table 1 shows that the traumatized animals to which 4-cyclopropylmethoxy-N-(3,5-dichloro-1-oxidopyridin-4-yl)-5-(methoxy)pyridine-2-carboxamide was administered curatively (group 3) reached the end of the balance beam more rapidly than the traumatized animals to which this compound was not administered (group 2).

Overall, these experiments show that the traumatized animals to which 4-cyclopropylmethoxy-N-(3,5-dichloro-1-oxidopyridin-4-yl)-5-(methoxy)pyridine-2-carboxamide was administered show a better re-establishment in terms of motor functions than the non-treated traumatized animals. The results are similar when the invention is administered preventively, i.e. prior to the trauma.

EXAMPLE 2

Evaluation of the effectiveness of ((4R)-4-[3-(cyclopentyloxy)-4-methoxyphenyl]pyrrolidine-2-one) in the treatment of spinal cord traumas:

An experiment similar to that of Example 1 was carried out by administering ((4R)-4-[3-(cyclopentyloxy)-4-methoxyphenyl]pyrrolidine-2-one) to 34-week-old OF1 mice (Charles River, France) weighing 12 to 14 g, in the treatment of spinal cord traumas.

((4R)-4-[3-(Cyclopentyloxy)-4-methoxyphenyl]-pyrrolidine-2-one), also called (R)-(−)-Rolipram, is in particular described in document U.S. Pat. No. 4,193,926.

The mice were tested in the beam balance test, according to operating conditions identical to those described above.

The following groups were formed:

Group A (no trauma) is composed of control animals which are not subjected to any trauma.

Group B (trauma alone) is composed of traumatized animals to which one dose per day of carrier (2% PEG 200) is administered.

Group C (trauma+active ingredient 0.03 mg/kg at +4 hours) receives a solution containing (R)-(−)-Rolipram (0.03 mg/kg) in the carrier (2% PEG 200), orally, 4 hours and 6 hours after the lesion, and then daily, orally, for 4 weeks after the trauma.

The results obtained for each group of mice are expressed as percentage (%) deficiency of motor functions in the traumatized mice compared with the non-traumatized mice:

To do this, the difference in time taken between the group of mice tested to which (R)-(−)-Rolipram was administered (group C) and the group of non-traumatized mice (group A) is measured and expressed as a percentage relative to the difference in time taken between the traumatized mice to which one dose per day of carrier was administered (group B) and the time taken by the non-traumatized mice (group A). This ratio therefore gives the percentage deficiency in motor functions of the traumatized mice compared with the non-traumatized mice.

This calculation of the percentage deficiency of the mice tested is performed according to the following formula:

% deficiency of group (c)=[(mean of the travel time of group C)−(mean of the travel time of group A)]/[(mean of the travel time of group B)−(mean of the travel time of group A)]

with:
group A: non-traumatized animals
group B: traumatized animals treated with the carrier
group C: traumatized animals treated with (R)-(−)-Rolipram The higher the percentage expressed, the greater the motor function deficiency observed. Thus, a result of 100% (one hundred percent) corresponds to a group of traumatized mice on which no therapeutic effect is observed.

A value greater than 100% indicates that the group of mice evaluated took, on average, more time to travel the distance than that taken, on average, by the group of traumatized mice treated with the vehicle.

The results obtained for each group of mice are reported in Table 2:

TABLE 2

Results on the balance beam test for groups A to C:

| Groups | Travel time (% motor function deficiency) | | | | | | |
|---|---|---|---|---|---|---|---|
| | D = 0 Trauma | D + 2 | D + 7 | D + 14 | D + 21 | D + 28 | Mean |
| A: (no trauma) | No | 0 | 0 | 0 | 0 | 0 | 0 |
| B: (trauma alone) | Yes | 100 | 100 | 100 | 100 | 100 | 100 |
| C: (trauma + (R)-(−)-Rolipram (0.03 mg/kg po at +4 h)) | Yes | 110 | 67 | 48 | 122 | 108 | 91 |

These experiments show that the traumatized animals treated with (R)-(−)-Rolipram, even at administered doses 3 times greater than the administered doses of 4-cyclopropylmethoxy-N-(3,5-dichloro-1-oxidopyridin-4-yl)-5-(methoxy)pyridine-2-carboxamide, exhibit a motor function deficiency which is greater than that of the animals treated with 4-cyclopropylmethoxy-N-(3,5-dichloro-1-oxidopyridin-4-yl)-5-(methoxy)pyridine-2-carboxamide.

By way of comparison, the values obtained for the traumatized mice to which 4-cyclopropylmethoxy-N-(3,5-dichloro-1-oxidopyridin-4-yl)-5-(methoxy)pyridine-2-carboxamide was administered (group 3 of Table 1) are reported in Table 3 in the form of percentage motor function deficiency:

TABLE 3

Comparison of the results obtained for groups of mice 3 and C

| Groups | Travel time (% deficiency) | | | | | | |
|---|---|---|---|---|---|---|---|
| | D = 0 Trauma | D + 2 | D + 7 | D + 14 | D + 21 | D + 28 | Mean |
| C: (trauma + (R)-(−)-Rolipram (0.03 mg/kg po at +4 h)) | Yes | 110 | 67 | 48 | 122 | 108 | 91 |
| 3: (trauma + compound of the invention (0.01 mg/kg po at +4 h)) | Yes | 84 | 72 | 49 | 60 | 44 | 62 |

Group C: traumatized animals treated with (R)-(−)-Rolipram.
Group 3: traumatized animals treated with 4-cyclo-propylmethoxy-N-(3,5-dichloro-1-oxidopyridin-4-yl)-5-(methoxy)pyridine-2-carboxamide.

The animals treated with 4-cyclopropylmethoxy-N-(3,5-dichloro-1-oxidopyridin-4-yl)-5-(methoxy)pyridine-2-carboxamide exhibit a degree of motor function deficiency which is less than that of the animals treated with (R)-(−)-Rolipram.

EXAMPLE 3

Evaluation of the emetic effects of 4-cyclopropyl-methoxy-N-(3,5-dichloro-1-oxidopyridin-4-yl)-5-(methoxy)pyridine-2-carboxamide The emetic capacity of 4-cyclopropylmethoxy-N-(3,5-dichloro-1-oxidopyridin-4-yl)-5-(methoxy)pyridine-2-carboxamide was evaluated in the ferret. Two groups of ferrets were used, the first being given the carrier (PEG 200) and the second being given 4-cyclopropyl-methoxy-N-(3,5-dichloro-1-oxidopyridin-4-yl)-5-(methoxy)pyridine-2-carboxamide in solution in the carrier (PEG 200), by oral gavage, at doses of 0.05 mg/kg and 0.1 mg/kg. The animals were observed continually for the 2 hours following administration and then every hour up to 6 hours after administration. The clinical signs (in particular retching and vomiting) were noted.

When administered at 0.1 mg/kg, 4-cyclopropylmethoxy-N-(3,5-dichloro-1-oxidopyridin-4-yl)-5-(methoxy)pyridine-2-carboxamide induces no retching or vomiting in the 5 ferrets treated.

These results show that the administration of a therapeutic dose of 4-cyclopropylmethoxy-N-(3,5-dichloro-1-oxidopyridin-4-yl)-5-(methoxy)pyridine-2-carboxamide for treating spinal cord traumas does not cause any emetic effect.

EXAMPLE 4

Evaluation of the emetic effects of (R)-(−)-Rolipram (((4R)-4-[3-(cyclopentyloxy)-4-methoxyphenyl] pyrrolidine-2-one))

The emetic capacity of (R)-(−)-Rolipram was evaluated in the ferret. Two groups of ferrets were used, the first receiving the carrier (PEG200) and the second receiving 4-cyclopropylmethoxy-N-(3,5-dichloro-1-oxidopyridin-4-yl)-5-(methoxy)pyridine-2-carboxamide in solution in the carrier (PEG200), by oral gavage, at doses of 0.05 mg/kg and 0.1 mg/kg. The animals were observed continually for the 2 hours following administration and then every hour up to 6 hours after administration. The clinical signs were noted.

When administered at 0.05 mg/kg and 0.1 mg/kg, (R)-(−)-Rolipram induces vomiting in the ferrets treated.

The results of Examples 3 and 4 show that the administration of a therapeutic dose of (R)-(−)-Rolipram causes emetic effects.

Thus, 4-cyclopropylmethoxy-N-(3,5-dichloro-1-oxidopyridin-4-yl)-5-(methoxy)pyridine-2-carboxamide is of use in the preparation of a medicament for the treatment of nervous system traumas, in particular spinal cord traumas, such as, for example, traumas occurring during a fall, an impact or a car accident, or cerebral traumas, while at the same time avoiding possible emetic effects.

We claim:

1. A method for treating spinal cord trauma comprising administering to a patient in need thereof a pharmaceutically effective amount of 4-cyclopropylmethoxy-N-(3,5-dichloro-1-oxidopyridin-4-yl)-5-(methoxy) pyridine-2-carboxamide, or a hemihydrate, or an addition salt with an acid thereof, wherein the treatment does not cause emetic effect or induce retching or vomiting to the patient.

2. A method for treating spinal cord trauma comprising administering to a patient in need thereof a pharmaceutically effective amount of 4-cyclopropylmethoxy -N-(3,5-dichloro-1-oxidopyridin-4-yl)-5-(methoxy) pyridine-2-carboxamide, wherein the treatment does not cause emetic effect or induce retching or vomiting to the patient.

* * * * *